United States Patent [19]
Dalton

[11] Patent Number: 5,498,251
[45] Date of Patent: Mar. 12, 1996

[54] TISSUE PERFUSION CATHETER

[76] Inventor: Michael J. Dalton, 7350 N. Ridgeway, Skokie, Ill. 60076

[21] Appl. No.: 350,095

[22] Filed: Nov. 29, 1994

[51] Int. Cl.⁶ .................................................. A61M 25/00
[52] U.S. Cl. ...................... 604/282; 604/163; 604/264; 604/53
[58] Field of Search .................................. 604/282, 285, 604/264, 280, 96–103, 158–164, 239, 53, 30, 31, 118, 165–169, 171–173, 245–249, 258, 268, 43, 256

[56] References Cited

U.S. PATENT DOCUMENTS

| | | |
|---|---|---|
| 3,757,768 | 9/1973 | Kline . |
| 3,922,378 | 11/1975 | Kline . |
| 4,405,314 | 9/1983 | Cope . |
| 4,782,834 | 11/1988 | Maguire et al. . |
| 4,821,722 | 4/1989 | Miller et al. . |
| 4,994,033 | 2/1991 | Shockey et al. . |
| 5,021,044 | 6/1991 | Sharkawy . |
| 5,087,244 | 2/1992 | Wolinsky et al. . |
| 5,250,034 | 10/1993 | Appling et al. . |
| 5,313,377 | 5/1994 | Dalton . |

OTHER PUBLICATIONS

H. Brincker, M.D., Critical Reviews in Oncology/Hematology, 15 (1993) pp. 91–98.
S. Dev and G. Hoffmann, Cancer Treatment Reviews, 20 (1994) pp. 105–115.

*Primary Examiner*—C. Fred Rosenbaum
*Assistant Examiner*—Perry E. Van Over
*Attorney, Agent, or Firm*—Richard L. Hansen

[57] ABSTRACT

The invention provides a tissue perfusion catheter which includes a tightly wound coil spring having an exterior, fluid impervious sleeve extending from a proximal end up to a distal portion of the spring which terminates at a sealed distal tip. Connection of the proximal end of the catheter to a source permits perfusion of diseased tissue with a therapeutic fluid which oozes at a low rate from the unsealed distal portion, while avoiding tissue ingrowth tending to plug the catheter. Various combinations which include the catheter are also provided as are methods for its use.

20 Claims, 4 Drawing Sheets

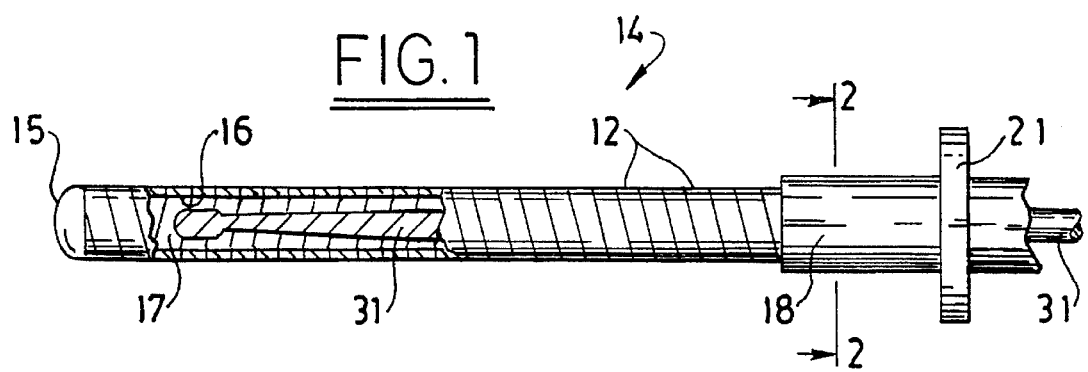
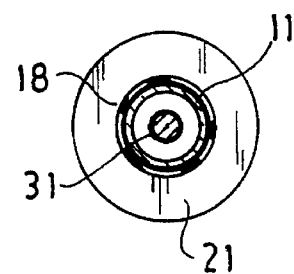
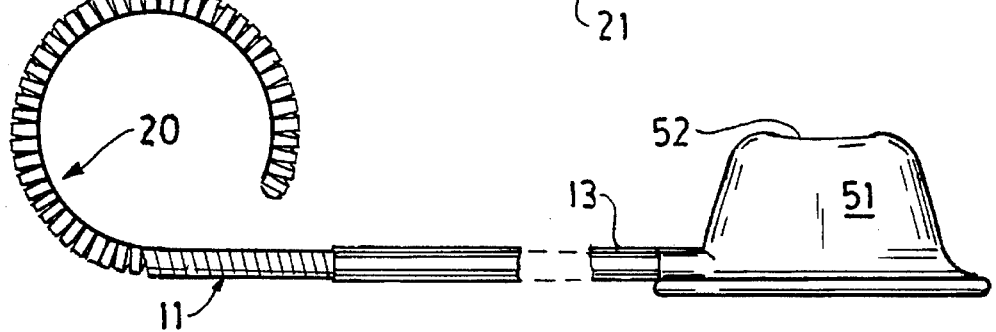
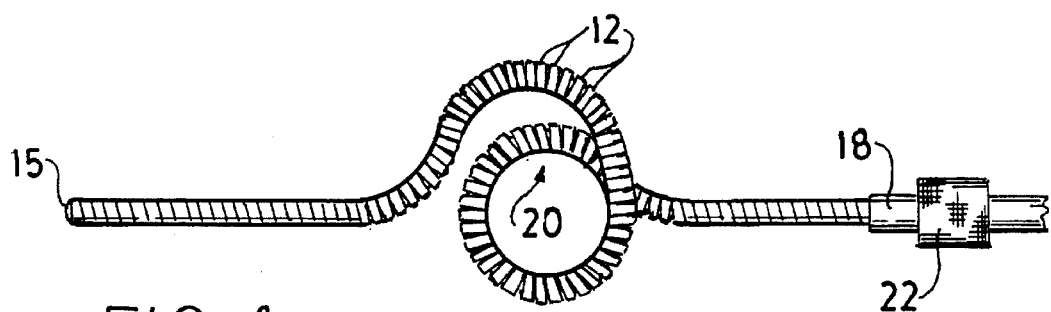

TISSUE PERFUSION CATHETER

This invention is in the field of medical devices, especially devices for delivering a therapeutic fluid to a selected site in the body; more particularly, this invention is related to a catheter, optionally in combination with other elements, for locally infusing a diseased tissue site with medication.

BACKGROUND

A number of medical procedures have been developed which access the vascular system. Such procedures include arteriography, aortography, angiography, and angioplasty, for example. Catheters of many different designs have been developed for these procedures.

The complexity of some of these catheter devices has made it difficult to pass them down the often tortuously convoluted paths of blood vessels. Consequently, additional tools have been developed for the purpose of aiding the passage of a catheterization device through the vessel. Among these devices are guidewires available commercially from various vendors.

Typically, the vascular system is accessed with an introducer which can be a relatively large bore hypodermic needle. The guidewire is passed down the needle bore into the vessel and is threaded through the vessel. The introducer needle is then withdrawn. To assist in passing the guidewire through the vessel, it may be equipped with means to stiffen it and/or steer the tip around curves in the vessel. When the tip of the guidewire is at the desired location, the catheter can be passed over the guidewire to the site. With the catheter in place, the guidewire can be withdrawn, and the procedure requiring the conduit for the catheterization can be carried out.

Commercially available guidewires constructed for the purpose just described are typically a few hundredths of an inch in diameter and consist of an elongated, flexible, tightly wound helical coil spring. A wire stylet carried within the lumen of the coil can be used to stiffen and steer it. The guidewire is typically made of stainless steel with a rounded and polished end weld closure.

Such helical coil springs, like those serving as guidewires in the aforesaid applications, can also be adapted, by simply leaving the end open, to function as flexible infusion wires to deliver contrast media for radiographic identification or other liquid to a selected site in the body. These devices are also available in commerce. They generally deliver a liquid at the rate of about 1–3 ml/sec under pressures in the range of about 0–250 psi; flow is out through the open end only.

The catheter of this invention is designed to facilitate the slow infusion delivery of a therapeutic fluid at a distant localized site of diseased tissue. The inventive catheter utilizes, as one of its elements, a helical coil spring guidewire with a sealed distal tip. Several pieces of prior art disclose catheterization devices which utilize guidewire-like structures.

U.S. Pat. No. 3,757,768 discloses a helical coil spring guidewire adapted for use as a catheter by including an inert plastic material on the entire outer surface of the spring which extends beyond the distal end of the spring to define a hollow tip which is perforated to deliver a fluid.

U.S. Pat. No. 3,922,378 is closely related to the aforesaid '768 patent in that it describes a method for applying a fluorinated hydrocarbon film to a flexible coil spring guidewire.

U.S. Pat. No. 4,405,314 discloses the use of a guidewire having a J-curvature at its distal end in conjunction with an introducer to enlarge a drainage tract created in the performance of a percutaneous nephrostomy. The guidewire is not the source of a medicament.

U.S. Pat. No. 4,821,722 describes a self-venting balloon dilatation catheter which utilizes at its distal tip a coil spring which has attributes of the guidewire described hereinabove, but it does not deliver a therapeutic fluid.

U.S. Pat. No. 4,994,033 discloses an intravascular catheter designed to apply liquid medication to a stenotic lesion in a blood vessel. The catheter is equipped with a guidewire which plays no direct role in delivering the medication.

U.S. Pat. No. 5,021,044 describes a multilumen vascular catheter for the delivery of a thrombolytic fluid to a blood vessel. The catheter is equipped with a central guidewire which facilitates advancement of the catheter in the blood vessel but is not directly involved in delivery of the therapeutic fluid.

U.S. Pat. No. 5,087,244 describes a catheter for the localized slow delivery of a medication through a balloon having minute holes in it. The catheter includes a central guidewire which has no direct role in delivering the medication.

Whereas elongated, flexible, tightly wound helical coil springs are disclosed in several capacities within the catheter context, none of these disclosures suggests the adaptation of such a helical coil spring for the slow, localized perfusion of a diseased tissue site with a therapeutic fluid. The medical literature suggests that such localized perfusion of diseased tissue can offer distinct advantages over other treatments.

For example, in the field of oncology, the use of chemotherapy systemically in the treatment of cancers is limited in many cases to utilizing very low concentrations of the therapeutic agent because of the cytotoxicity of the fluid when it is delivered into the blood stream. Direct intratumoral or loco-regional chemotherapy may permit the use of much higher concentrations of the therapeutic agent. In addition, bolus injections of the therapeutic agent, leading to spikes and valleys in the concentration of the medication over time may be avoided by continuously perfusing the tumorous region with the drug. In spite of these logical advantages, localized intratumoral chemotherapy has been largely overlooked.

In this regard, attention is directed to H. Brincker, M.D., *Critical Reviews in Oncology/Hematology*, 15 (1993) pp 91–98, in which the point is made that intratumoral chemotherapy is not even mentioned in major standard textbooks on chemotherapy and cancer treatment. Among the results of clinical studies summarized in this article are the following: Randomized trials involving a total of 411 patients with hepatic metastases from colorectal carcinoma showed significantly higher response and survival rates with intrahepatic as opposed to systemic infusion with the cancer drug FUDR. Intratumoral injections of the cytostatic agent thio-TEPA in 131 patients with advanced breast cancer resulted in improvement in 66% of the cases, while administration by the i.v. route was less effective.

Furthermore, it is reported that several studies of the intratumoral injection of bleomycin in patients with head and neck tumors have shown very promising results. Treatment of a variety of inoperable, deep-seated intraabdominal tumors with various chemotherapeutic agents injected directly into the tumors also led to promising results without systemic toxicity. The author of the aforesaid article concludes that "Both clinical and experimental studies show consistently that intratumoral chemotherapy leads to consistently higher concentrations of cytostatics in the target tissues than conventional i.v. chemotherapy, thus confirming the rationale for this treatment."

It is to be expected that increasing the local concentration of the therapeutic agent in the treatment of other types of diseased tissue will also lead to improved results. For example, it is likely that localized perfusion with an appropriate therapeutic agent will also improve the cure rate in the treatment of non-healing, ulcerous wounds.

Electrochemotherapy (ECT) and electrical impulse chemotherapy (EIC), in which a cancerous tumor is treated with a chemotherapeutic agent in the presence of an electric field applied across the tumor, has also yielding very promising results; see, e.g., S. Dev and G. Hofmann, *Cancer Treatment Reviews*, 20 (1994) pp 105–115. Electrically conductive catheters, such as those disclosed herein, can play an important role in such therapy.

SUMMARY OF THE INVENTION

It is one of the objectives of this invention to provide means for perfusing a selected localized site of diseased tissue with a therapeutic fluid.

It is another objective of this invention to provide a catheter which is specifically adapted to provide such localized perfusion over an extended period of time.

It is still another object of this invention to provide, not only a catheter to attain the aforesaid objectives, but also other components comprising a complete diseased tissue perfusion system for the local-regional delivery of the agent.

In attaining these objectives, this invention provides a tissue perfusion catheter which includes a helical coil spring of the type described above, the proximal end of the spring being adapted to receive therapeutic fluid from a fluid source, the distal portion of the spring terminating in a sealed distal tip, the helical coil defining a fluid-pervious side wall encircling an interior, fluid-containing lumen. The catheter also includes an inert, flexible sleeve, which is impervious to the therapeutic fluid, covering the exterior of and sealing the side wall from the proximal end up to the distal portion of the helical coil spring. The distal portion of the spring is uncovered and delivers the therapeutic fluid slowly from between the helical coils.

In preferred embodiments of the tissue perfusion catheter, the distal portion of the catheter is provided with means for retaining the catheter in the tissue to be perfused.

One of the advantages of the catheter of this invention is that tissue ingrowth, which often plagues long term infusion procedures, is largely avoided.

The invention also provides a catheter set including the tissue perfusion catheter and a stylet carried in the lumen of the catheter, as well as a catheter introducer which includes the catheter set and means, such as a hollow needle and/or a secondary catheter, for introducing the tissue perfusion catheter of this invention. In addition, the invention provides a complete tissue perfusion system in which an infusion pump and/or a subcutaneous fluid delivery port are included.

Furthermore, the invention provides a method for treating a selected site of diseased tissue by perfusing the tissue with a therapeutic fluid delivered by a catheter of this invention.

This invention, including how to make and how to use the invention, will be clarified by reference to the drawings which accompany this specification and to the Detailed Description which follows. Several of the drawings show elements which are optional, but not required.

BRIEF DESCRIPTION OF THE DRAWINGS

FIG. 1 is a plan view, with a portion broken away, showing the distal portion of a tissue perfusion catheter and catheter set of this invention.

FIG. 2 is a sectional view taken along line 2—2 of FIG. 1.

FIG. 3 is a diagrammatic view illustrating a tissue perfusion system of this invention utilizing a tissue perfusion catheter having a certain contorted configuration in the distal portion.

FIG. 4 is a plan view of the distal portion of a tissue perfusion catheter of this invention having another contorted configuration in the distal portion.

DETAILED DESCRIPTION

Figure 5A:
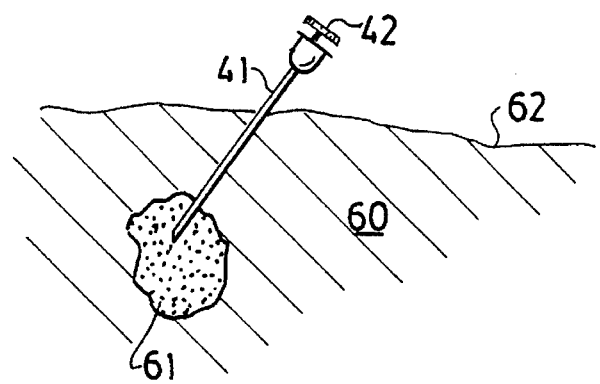
FIG. 5 is a sequence of diagrammatic views, partly in section, showing a catheter introducer of this invention and a method for treating a diseased tissue site with a tissue perfusion catheter of this invention.
Figure 5B:
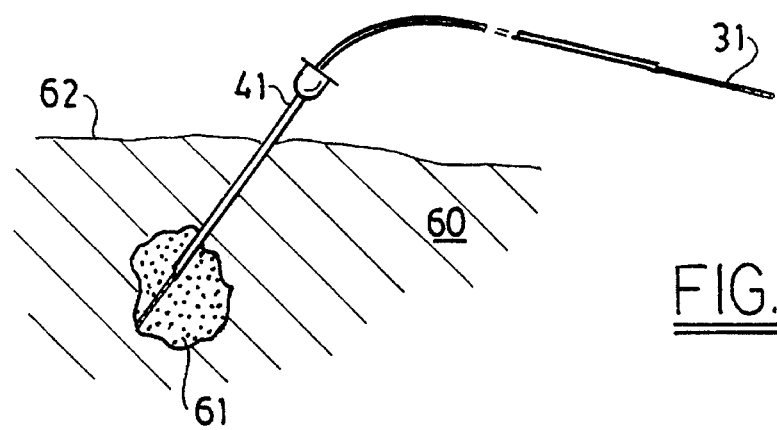
Figure 5C:
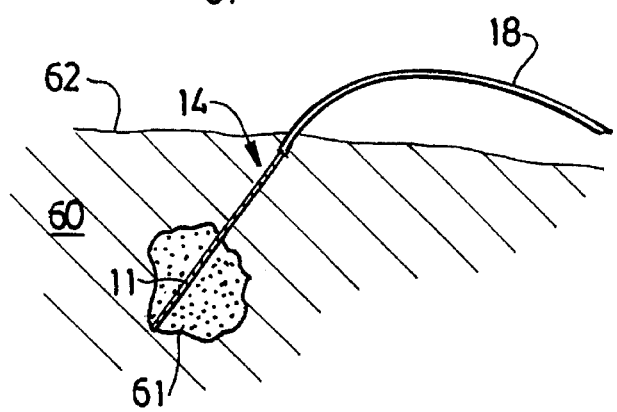
Figure 5D:
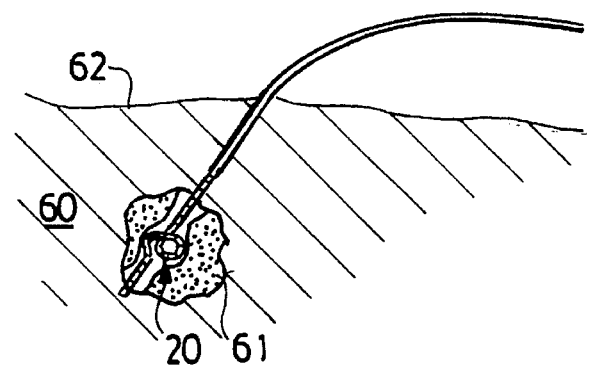

Tissue perfusion catheters of this invention are illustrated in FIGS. 1–4. The catheter includes an elongated, flexible, tightly wound helical coil spring 11 with windings 12. The catheter has a proximal end 13 to receive a therapeutic fluid from a source such as subcutaneous infusion port 51. If located close to the surface of the skin, the therapeutic fluid can be replenished periodically by hypodermic injection through septum 52. The catheter also has a distal portion 14 which terminates in a sealed distal tip 15. The helical coils define a side wall 16 encircling an interior, fluid-conducting lumen 17.

In contrast to the known guidewires and catheter adaptations of those guidewires, however, the tissue perfusion catheter of this invention includes an inert, flexible sleeve 18, a term used herein to include a coating, which is impervious to the therapeutic fluid and covers coil spring 11 exteriorly from its proximal end 13 up to, but not including, distal portion 14, thereby sealing side wall 16 against any fluid leakage for its entire length, except the distal portion 14 of the catheter.

In accordance with this invention, in spite of the fact that coil spring 11 is very tightly wound, with the spring windings 12 very closely spaced, a therapeutic fluid can be made to ooze slowly from the distal portion of the catheter. By implanting the distal portion of the catheter in diseased tissue, the tissue can be slowly perfused with a therapeutic fluid and thereby treated. The range in flow rate which is useful in this application is on the order of about 1 ml/day to about 20 ml/day. The flow rate can be controlled within this range using an external powered source, such as an infusion pump, by adjusting the timing of pressure pulses, for example. This flow rate is about 10,000 times lower than that associated with the open-ended infusion wires which are commercially available. The therapeutic fluid can be a cytostatic agent, an antibiotic, a growth hormone, a nutrient, etc., or any chemically compatible combination thereof.

The coil spring guidewire which is one element of the catheter of this invention is generally made of 300 series stainless steel and is available in lengths ranging to about 400 cm, with an outside diameter of about 0.02 inch to about 0.07 inch and an inside diameter of about 0.01 inch to about 0.06 inch, so that sidewall 16 can be about 0.01 inch thick. Guidewires in which the cross section of individual helical windings is either circular or rectangular are available. Guidewires suitable for use in this invention are available from Lake Region Manufacturing Co., Chaska, Minn., for example.

In preferred embodiments of the invention, the helical coil spring has individual windings which are rectangular in cross section; i.e., the coils are flat. Such coil springs have a higher ID/OD ratio and a smoother surface, so they pass more easily down a blood vessel or through tissue, and there is more contact area between the individual windings than in coil springs in which the windings are circular in cross section, making the side wall less permeable to fluid. In addition, the sidewall is more resistant to tissue ingrowth if the windings are rectangular in cross section.

Another element of the catheter is an inert, flexible sleeve applied to the exterior of the coil spring, extending from the proximal end of the spring to the distal portion. It is a function of this sleeve to seal the coil spring against leakage of the therapeutic fluid, except in the distal portion. Generally, the sleeve can be a suitable polymeric material.

The sleeve element, which can be introduced by any of a number of acceptable methods, can be a coating, for example, which can be added by sealing off the proximal end of the coil spring and dipping it into a solution or melt of the desired coating material up to the desired point, removing the spring, and then drying or cooling it. Alternatively, the sleeve can be added by inserting the spring into tubing having a slightly larger ID than the OD of the coil spring and shrinking the tubing onto the spring. In pursuing this alternative, tubing made of a suitable polymer can be swollen by soaking it in a solvent; the coil spring is then slipped into the swollen tubing and the solvent evaporated, shrinking the tubing about the spring.

The sleeve material is preferably a biocompatible polymer which is impervious to the therapeutic fluid. Candidates, depending upon the nature of the therapeutic fluid, include polyisoprene, poly(styrene-co-butadiene), polyisobutylene, polychloroprene, poly(butadiene-co-acrylonitrile), polysulfides, polyurethanes, polyacrylates, polysiloxanes, i.e., silicones, and fluorocarbon polymers, such as polytetrafluoroethylene and poly(fluorovinylsilane).

Among these candidates, silicone polymers, polytetrafluoroethylene (TEFLON) and polyurethanes are preferred. Tubing made of the silicone polymer known as "RX-65" available from Dow-Corning, Midland, Mich. is especially useful. It can be swollen in a fluorocarbon solvent prior to inserting the coil spring. Subsequent evaporation of the fluorocarbon causes the tubing to form a flexible, fluid-impervious, biocompatible sleeve over the spring. The sleeve should be as thin and flexible as possible. A sleeve thickness of about 0.005–0.01 inch is generally satisfactory, but variations outside this range can also be acceptable.

Although straight catheters, made using straight coil springs, are useful in a number of applications, in other cases it is advantageous to introduce a kink into the distal portion of the catheter which urges the catheter to bend and assume a contorted configuration. Guidewires having "J-shaped" ends can be obtained in commerce. The J-shaped ends, in which the spring is bent about a radius of about 1.5–15 mm, assist in steering the guidewires through blood vessels.

Permanent kinks in coil springs, leading to contortions of various shapes, can be produced in guidewires by thermal treatment, or they can be obtained conveniently on a custom order basis from guidewire manufacturers. Two exemplary types of contortions 20, especially useful in the catheter of this invention, are shown in FIGS. 3 and 4, respectively.

The circular contortion shown in FIG. 3 is especially useful in treating non-healing ulcerous wounds by long term infusion with antibiotics, growth hormones or nutrients, for example. In this application the circular contortion is about 1–5 cm in diameter. FIG. 4 illustrates another useful contortion, a complete loop which is especially useful as one means of retaining the distal end of the catheter in the diseased tissue, e.g., anchored in a tumor, as explained hereinafter.

This invention also provides a catheter set which includes the catheter described above in combination with a stylet 31 as seen in FIG. 1. Stylet 31 is a substantially straight, stiff member. The stylet generally extends from or beyond the proximal end of the catheter into the distal portion. The inserted stylet stiffens the catheter and enables the catheter to be guided down a blood vessel or through a needle into the desired tissue. If the catheter is made with a kink in the distal portion thereof, the stylet inserted past the kink in the spring will straighten out the contortion urged into the coil spring by the permanent kink.

In addition, the invention provides a catheter introducer which includes the catheter set described immediately above in combination with means for introducing the catheter of this invention into the tissue situs requiring treatment. A fairly large bore needle, about 15–18 gauge, which can optionally also include a trocar, will generally be employed to create a channel into the tissue through which a catheter can be inserted. One way in which the catheter introducer can be used to perfuse a region of diseased tissue is illustrated in FIG. 5. In FIG. 5, tissue 60, which in this case lies near the surface of skin 62, contains a region of diseased tissue 61, which, for purposes of this illustration, is a soft, pliable tumor.

In FIG. 5(a), a hollow 15 gauge Touhy needle 41 carrying a pencil point trocar 42 is inserted through the skin and into the tumor. The procedure can be monitored radiographically. After removal of the trocar, in (b) a catheter set of this invention, i.e., catheter and stylet, is inserted into the needle, creating a catheter introducer of this invention. The catheter set is pushed through the tumor, so that there is some of the distal portion 14 of the catheter on both sides of the tumor. The distal portion of the catheter has been kinked in manufacture and thereby urged to assume the contortion shown in FIG. 4. When the stylet is removed as in (c) the proximal end of the catheter is connected to a source of therapeutic fluid, such as an external infusion pump, and the tumor continuously perfused over a period of time. The kink in the catheter urges the distal portion to assumed a contorted configuration, thereby continuing to press the catheter against the tissue, anchoring the distal portion in the tumor. As shown in (d), over time, as the tumor tissue becomes necrotic, the contortion expands to maintain the location of the distal portion of the catheter in the tumor. Ultimately, the remains of the dead tumor can be removed surgically. Had the tumor been solid and rigid, a catheter with a straight distal portion and no kink could have been chosen.

There are means, other than a kink in the distal portion of the catheter, by which the catheter can be retained in the tissue to be treated. For example, the catheter can be fitted with a suture ring or flange around the catheter, such as suture flange 21, an optional feature shown in FIGS. 1 and 2. Stitches through the flange and adjacent tissue hold the catheter in place. The suture flange can be a silicone member, optionally reinforced with a fabric scrim and permanently affixed to the catheter. A catheter equipped with a suture flange for anchoring it can be used effectively in conjunction with a laparoscope as the means for introducing the catheter. A suture flange anchoring means is also effectively used in situations in which the mass of the tumor is very large and the tumor is not easily removed by surgery.

In other cases, the catheter of this invention can be equipped with a tissue ingrowth cuff, such as is shown as optional element 22 in FIG. 4, in order to retain the distal portion of the catheter in the diseased tissue. The cuff is advantageously made of a matrix of polyester fibers, such as Dacron polyester. In this application, the cuff is of the order of about 5 mm in length and about 1 mm thick, the dimensions being selected to allow the catheter to pass through an introducer and the catheter to be released from the ingrown tissue with a slight tug or pull on the catheter. It will be evident that the catheter of this invention can be employed without any specific means for anchoring it in the tissue or with one or a combination of means for anchoring it, depending upon the specific nature of the tissue site to be perfused.

The catheter of this invention can be inserted into the diseased tissue site in a number of ways other than by the percutaneous technique illustrated in FIG. 5. It can be inserted through the vascular system, for example, and by other procedures already well known to those skilled in the art. For example, if the diseased tissue is deeply lying in the body, where percutaneous access with a needle is impractical, a guidewire can be inserted through the venous system to a site near the diseased tissue, followed over the guidewire by an introducer catheter larger in ID than the OD of the catheter set. After removal of the guidewire, a catheter set of this invention can be inserted, with radiographic assistance, through the introducer catheter and into or through the diseased tissue. After optionally creating a venous block at the end of the introducer catheter by injection of a hemostatic agent, the introducer catheter can be removed, as can the stylet, and continuous perfusion of the diseased tissue with a therapeutic fluid can be initiated.

The use of a balloon catheter as a component of the introducer of this invention can prove to be especially advantageous in that it can be used as a means for preparing the diseased tissue site to more effectively utilize the tissue perfusion catheter and/or also as a means for anchoring the tissue perfusion catheter at the desired site. When employed as a component of the introducer, the balloon catheter is a secondary catheter used in combination with a catheter set of this invention; i.e., in combination with a tissue perfusion catheter of this invention and a stylet. Generally, a hollow needle is also a component of the introducer.

Figure 6:
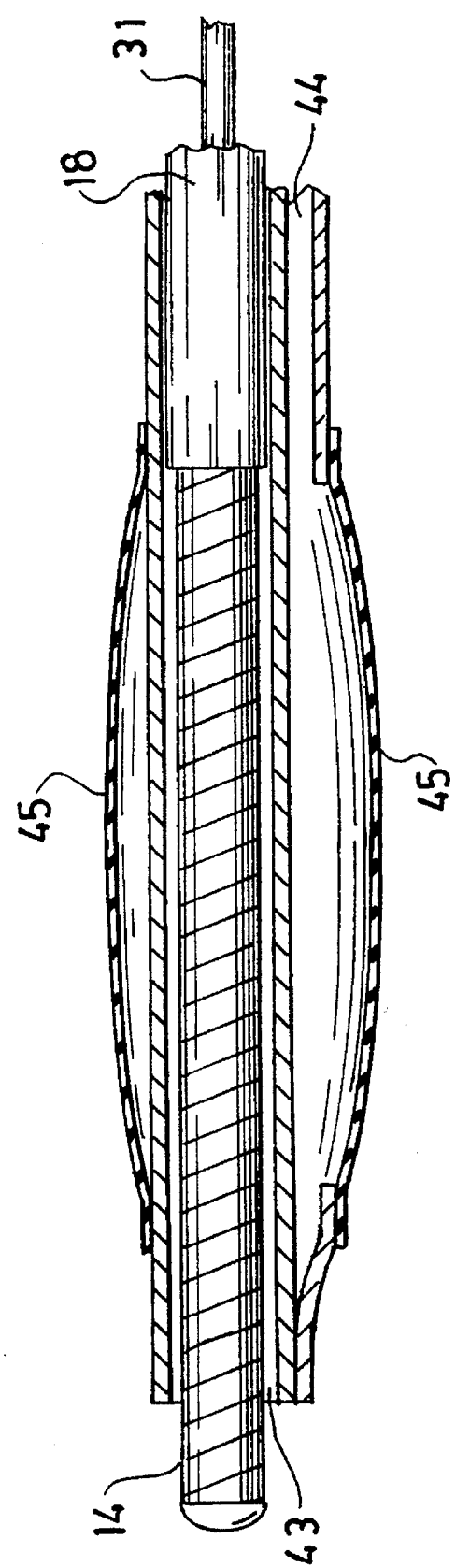
FIG. 6 is a plan view showing the distal portion of a tissue perfusion catheter of this invention in combination with a secondary catheter, shown in section, for introducing the tissue perfusion catheter.
Figure 7A:
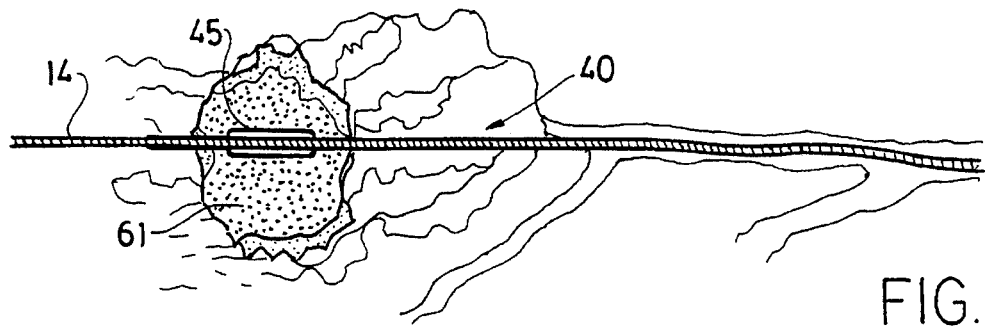
FIG. 7 is a sequence of diagrammatic views, partly in section, showing the use of the combination of FIG. 6 to treat a diseased tissue site.
Figure 7B:
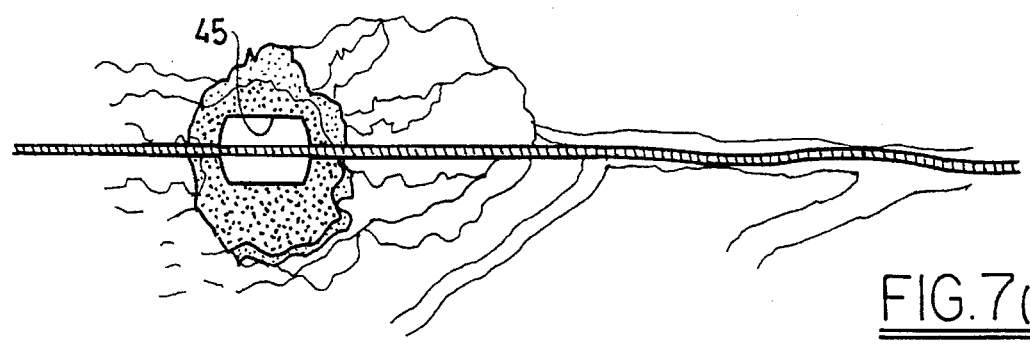
Figure 7C:
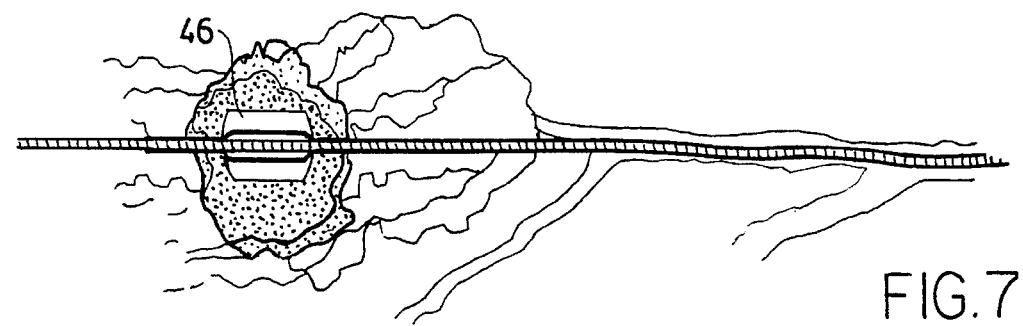
Figure 7D:
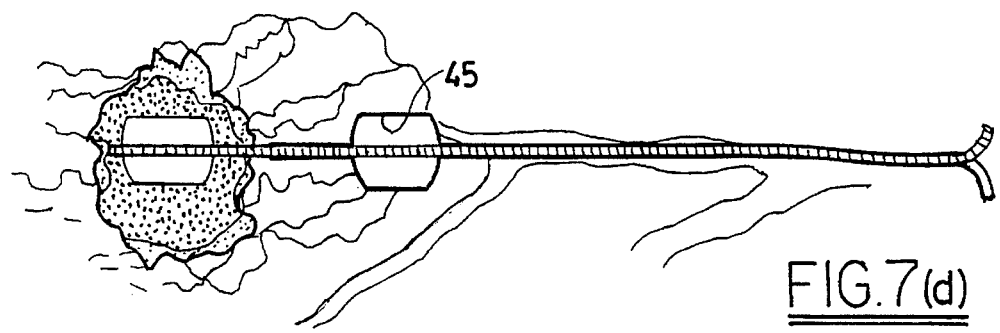

FIG. 6 illustrates a typical dual lumen balloon catheter in combination with a tissue perfusion catheter of this invention. A balloon catheter similar to that shown in FIG. 6 is disclosed in U.S. Pat. No. 4,782,834 and is of a type well known to those skilled in the art, any of which may be satisfactorily employed. In FIG. 6, primary lumen 43 of the balloon catheter contains the distal portion 14 of the tissue perfusion catheter with sleeve 18 and is equipped with stylet 31. The secondary lumen 44 of the balloon catheter terminates in balloon 45, which is shown slightly pressurized and forms a toroid about the tissue perfusion catheter.

Use of the balloon catheter as an introducer component is shown in FIG. 7. In FIG. 7(a), introducer 40 has been inserted into tumor 61, previously accessed with a hollow needle, so that the distal portion 14 of the catheter of this invention projects through the tumor, the stylet having been removed and balloon 45 of the secondary catheter remaining within the tumor. In (b), balloon 45 is distended, creating cavity 46 in the tumor, as shown in FIG. 7(c). Introducer 40 is then withdrawn slightly, placing the distal portion 14 of the perfusion catheter within the tumor, where perfusion can take place into the cavity provided for the medication, while reinflation of balloon 45 serves as a means for retaining the distal portion of the perfusion catheter in place.

In a tissue perfusion system according to this invention the source of therapeutic fluid can be an implanted infusion port with hypodermic needle replenishment as shown in FIG. 3, with or without an external infusion pump. Alternatively, the tissue perfusion catheter can be connected directly to a source of medication external to the body. For example, a compression fitting can be used to make the connection if it is internal, and a Luer lock fitting, such as is described in U.S. Pat. No. 5,312,377, for example, can be employed if the connection is made externally.

It is not intended that the invention be limited to the aforesaid text and drawings, but rather the invention is limited only by the scope of the following claims.

What is claimed is:

1. A tissue perfusion catheter comprising
   (a) an elongated, flexible, tightly wound, normally compressed helical coil spring having a proximal end to receive therapeutic fluid from a source and a distal portion terminating in a sealed distal tip, said helical coil spring defining a fluid-pervious side wall encircling an interior, fluid-conducting lumen; and
   (b) an inert, flexible sleeve, impervious to the therapeutic fluid, exteriorly covering and sealing that part of the side wall from the proximal end to, but not including, the distal portion of said spring;
   whereby therapeutic fluid entering the proximal end of the catheter is conducted to the distal portion of said spring, where it oozes from the catheter, perfusing the tissue region.

2. The tissue perfusion catheter of claim 1 further comprising means for retaining the distal portion of said spring in the tissue region.

3. The tissue perfusion catheter of claim 1 further comprising means for retaining the distal portion of said spring in the tissue region, which means comprises at least one permanent kink in the distal portion of said spring, thereby urging said spring to assume a contorted configuration.

4. The tissue perfusion catheter of claim 1 further comprising means for retaining the distal portion of said spring in the tissue region, said means being selected from the group consisting of at least one permanent kink in the distal portion of said spring, at least one suture flange fitted to the catheter, at least one tissue ingrowth cuff affixed to the catheter, and a secondary balloon catheter.

5. A catheter set comprising
   (1) a tissue perfusion catheter which includes
      (a) an elongated, flexible, tightly wound, normally compressed helical coil spring having a proximal end to receive therapeutic fluid from a source and a distal portion terminating in a sealed distal tip, said helical coil spring defining a fluid-pervious side wall encircling an interior, fluid-conducting lumen; and
      (b) an inert, flexible sleeve, impervious to the therapeutic fluid, exteriorly covering and sealing that part of the side wall from the proximal end to, but not including, the distal portion of said spring; together with (2) a substantially straight, stiff stylet carried within the catheter lumen.

6. A catheter set of claim 5 further comprising at least one permanent kink in the distal portion of said spring, thereby urging said spring to assume a contorted configuration; whereby said stylet extended beyond said kink straightens the catheter.

7. A catheter introducer comprising
   (1) a tissue perfusion catheter which includes
      (a) an elongated, flexible, tightly wound, normally compressed helical coil spring having a proximal end to receive therapeutic fluid from a source and a distal portion terminating in a sealed distal tip, said helical coil spring defining a fluid-pervious side wall encircling an interior, fluid-conducting lumen; and
      (b) an inert, flexible sleeve, impervious to the therapeutic fluid, exteriorly covering and sealing that part of the side wall from the proximal end to, but not including, the distal portion; in combination with
   (2) means for introducing the catheter into the tissue to be perfused.

8. The catheter introducer of claim 6 wherein the means for introducing the catheter includes a hollow needle.

9. The catheter introducer of claim 7 further comprising means for retaining the distal portion of said spring in the tissue region, wherein the means for introducing the catheter and the means for retaining said distal portion of said spring in the tissue region both include a secondary catheter which is a balloon catheter.

10. The catheter introducer of claim 6 further comprising at least one permanent kink in said distal portion urging said spring to assume a contorted configuration; and
    a substantially straight, stiff stylet extended into the lumen and past any kink in the distal portion;
    whereby said stylet extended beyond said kink straightens the catheter.

11. A tissue perfusion system comprising
    (1) a tissue perfusion catheter which includes
       (a) an elongated, flexible, tightly wound, normally compressed helical coil spring having a proximal end to receive therapeutic fluid from a source and a distal portion terminating in a sealed distal tip, said helical coil spring defining a fluid-pervious side wall encircling an interior, fluid-conducting lumen;
       (b) an inert, flexible sleeve, impervious to the therapeutic fluid, exteriorly covering and sealing that part of the side wall from the proximal end to, but not including, the distal portion of said spring; together with
    (2) a source of therapeutic fluid connected to the proximal end of the catheter.

12. The tissue perfusion system of claim 11 further comprising means for retaining the distal portion of said spring in the tissue region.

13. The tissue perfusion system of claim 11 further comprising means for retaining said distal portion of said spring in the tissue region, said means being selected from the group consisting of at least one permanent kink in the distal portion of said spring, at least one suture flange fitted to the catheter, at least one tissue ingrowth cuff affixed to the catheter, and a secondary balloon catheter.

14. A method for perfusing a diseased tissue site with a therapeutic fluid which comprises
    (a) providing a tissue perfusion catheter which includes
       (1) an elongated, flexible, tightly wound helical coil spring having a proximal end to receive therapeutic fluid from a source and a distal portion terminating in a sealed distal tip, said helical coil spring defining a fluid-pervious side wall encircling an interior, fluid-conducting lumen; and
       (2) an inert, flexible sleeve, impervious to the therapeutic fluid, exteriorly covering and sealing that part of the side wall from the proximal end to the distal portion;
    (b) introducing the distal portion of said catheter into the diseased tissue; and
    (c) connecting the proximal end of said catheter to a source of the therapeutic fluid.

15. The method of claim 14 wherein the source of the therapeutic fluid is a drug delivery port connected to the proximal end of said catheter, implanted near the skin, and filled with the therapeutic fluid periodically by hypodermic injection.

16. The method of claim 14 wherein the tissue perfusion catheter is introduced by using means which include a balloon catheter.

17. The method of claim 14 wherein the source of the therapeutic fluid is an external infusion pump connected to the proximal end of said catheter led through the skin.

18. The method of claim 14 wherein the distal portion of said catheter is inserted into the diseased tissue transdermally by means of an introducer comprising a hollow needle.

19. The method of claim 14 wherein the distal portion of said catheter is inserted into the diseased tissue through the venous system using an introducer catheter.

20. The method of claim 14 in which the catheter is inserted into the body with a laparoscope.

* * * * *